(12) United States Patent
Allen (10) Patent No.: US 7,591,848 B2
(45) Date of Patent: Sep. 22, 2009

(54) RIVETED STENT VALVE FOR PERCUTANEOUS USE

(75) Inventor: Jeffrey W. Allen, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 334 days.

(21) Appl. No.: 11/278,856

(22) Filed: Apr. 6, 2006

(65) Prior Publication Data

US 2007/0239273 A1    Oct. 11, 2007

(51) Int. Cl.
*A61F 2/24* (2006.01)
(52) U.S. Cl. .................................. 623/2.17; 623/2.1
(58) Field of Classification Search ....... 623/1.24–1.26, 623/2.1–2.17
See application file for complete search history.

(56) References Cited

U.S. PATENT DOCUMENTS

| | | |
|---|---|---|
| 3,334,629 A | 8/1967 | Cohn |
| 3,540,431 A | 11/1970 | Mobin-Uddin |
| 3,628,535 A | 12/1971 | Ostrowsky et al. |
| 3,642,004 A | 2/1972 | Osthagen et al. |
| 3,657,744 A | 4/1972 | Esek |
| 3,671,979 A | 6/1972 | Moulopoulos |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,056,854 A | 11/1977 | Boretos et al. |
| 4,106,129 A | 8/1978 | Carpentier et al. |
| 4,233,690 A | 11/1980 | Akins |
| 4,291,420 A | 9/1981 | Reul |
| 4,425,908 A | 1/1984 | Simon |
| 4,501,030 A | 2/1985 | Lane |
| 4,580,568 A | 4/1986 | Gianturco |
| 4,610,688 A | 9/1986 | Silvestrini et al. |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |
| 4,733,665 A | 3/1988 | Palmaz |

(Continued)

FOREIGN PATENT DOCUMENTS

EP    1057459    2/2000

(Continued)

OTHER PUBLICATIONS

P. Bonhoeffer, MD, et al., "Transcatheter Implantation of a Bovine Valve in a Pulmonary Position—A Lamb Study," pp. 8-3-816; Aug. 2000.

(Continued)

*Primary Examiner*—Suzette J Gherbi (57) ABSTRACT

A system and method for treating a vascular condition includes a conduit having an inner wall defining lumen and a replacement valve device. The replacement valve device includes a prosthetic valve connected to an expandable support structure; the expandable support structure includes at least one valve attachment portion and a plurality of valve attachment devices. Each valve attachment portion includes a plurality of struts, each strut having at least one opening for receiving one of the plurality of valve attachment devices.

19 Claims, 9 Drawing Sheets

U.S. PATENT DOCUMENTS

| | | |
|---|---|---|
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,909,252 A | 3/1990 | Goldberger |
| 4,917,102 A | 4/1990 | Miller et al. |
| 4,954,126 A | 9/1990 | Wallsten |
| 4,994,077 A | 2/1991 | Dobben |
| 5,002,559 A | 3/1991 | Tower |
| 5,156,621 A | 10/1992 | Navia et al. |
| 5,161,547 A | 11/1992 | Tower |
| 5,163,953 A | 11/1992 | Vince |
| 5,197,979 A | 3/1993 | Quintero et al. |
| 5,217,483 A | 6/1993 | Tower |
| 5,332,402 A | 7/1994 | Teitelbaum et al. |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,431,676 A | 7/1995 | Dubrul et al. |
| 5,507,767 A | 4/1996 | Maeda et al. |
| 5,545,211 A | 8/1996 | An et al. |
| 5,554,185 A | 9/1996 | Block et al. |
| 5,575,818 A | 11/1996 | Pinchuk |
| 5,645,559 A | 7/1997 | Hachtman et al. |
| 5,667,523 A | 9/1997 | Bynon et al. |
| 5,674,277 A | 10/1997 | Freitag |
| 5,695,498 A | 12/1997 | Tower |
| 5,713,953 A | 2/1998 | Vallana et al. |
| 5,800,456 A | 9/1998 | Maeda et al. |
| 5,817,126 A | 10/1998 | Imran |
| 5,824,043 A | 10/1998 | Cottone, Jr. |
| 5,824,053 A | 10/1998 | Khosravi et al. |
| 5,824,056 A | 10/1998 | Rosenberg |
| 5,824,064 A | 10/1998 | Taheri |
| 5,840,081 A | 11/1998 | Andersen et al. |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,907,893 A | 6/1999 | Zadno-Azizi et al. |
| 5,925,063 A | 7/1999 | Khosravi |
| 5,944,738 A | 8/1999 | Amplatz et al. |
| 5,954,766 A | 9/1999 | Zadno-Aziz et al. |
| 5,957,949 A | 9/1999 | Leonhardt et al. |
| 5,984,957 A | 11/1999 | Laptewicz, Jr. et al. |
| 6,001,126 A | 12/1999 | Nguyen-Thien-Nhon |
| 6,027,525 A | 2/2000 | Suh et al. |
| 6,042,598 A | 3/2000 | Tsugita et al. |
| 6,051,014 A | 4/2000 | Jang |
| 6,123,723 A | 9/2000 | Konya et al. |
| 6,146,366 A | 11/2000 | Schachar |
| 6,162,245 A | 12/2000 | Jayaraman |
| 6,168,614 B1 | 1/2001 | Andersen et al. |
| 6,200,336 B1 | 3/2001 | Pavcnik et al. |
| 6,221,006 B1 | 4/2001 | Dubrul et al. |
| 6,221,091 B1 | 4/2001 | Khosravi |
| 6,241,757 B1 | 6/2001 | An et al. |
| 6,254,436 B1 | 7/2001 | Nitta et al. |
| 6,254,632 B1 * | 7/2001 | Wu et al. ............... 623/1.15 |
| 6,258,114 B1 | 7/2001 | Konya et al. |
| 6,258,115 B1 | 7/2001 | Dubrul et al. |
| 6,258,120 B1 | 7/2001 | McKenzie et al. |
| 6,277,555 B1 | 8/2001 | Duran et al. |
| 6,309,417 B1 | 10/2001 | Spence et al. |
| 6,327,772 B1 | 12/2001 | Zadno-Aziz et al. |
| 6,338,735 B1 | 1/2002 | Stevens |
| 6,342,070 B1 | 1/2002 | Nguyen-Thien-Nhon |
| 6,348,063 B1 | 2/2002 | Yassour et al. |
| 6,350,282 B1 | 2/2002 | Eberhardt |
| 6,352,708 B1 | 3/2002 | Duran et al. |
| 6,364,905 B1 | 4/2002 | Simpson et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,509,930 B1 | 1/2003 | Hirano et al. |
| 6,527,800 B1 | 3/2003 | McGuckin, Jr. et al. |
| 6,530,949 B2 | 3/2003 | Konya et al. |
| 6,530,952 B2 * | 3/2003 | Vesely ................... 623/2.18 |
| 6,558,417 B2 | 5/2003 | Peredo |
| 6,562,058 B2 | 5/2003 | Seguin et al. |
| 6,569,196 B1 | 5/2003 | Vesely |
| 6,592,546 B1 | 7/2003 | Barbut et al. |
| 6,622,604 B1 | 9/2003 | Chouinard et al. |
| 6,632,243 B1 | 10/2003 | Zadno-Azizi et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,702,851 B1 | 3/2004 | Chinn et al. |
| 6,719,789 B2 | 4/2004 | Cox |
| 6,730,118 B2 * | 5/2004 | Spenser et al. ............. 623/1.24 |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,887,266 B2 | 5/2005 | Williams et al. |
| 6,890,330 B2 | 5/2005 | Streeter et al. |
| 6,896,690 B1 | 5/2005 | Lambrecht et al. |
| 6,929,653 B2 | 8/2005 | Streeter |
| 7,011,681 B2 * | 3/2006 | Vesely ................... 623/2.11 |
| 2001/0007956 A1 | 7/2001 | Letac et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2002/0032480 A1 | 3/2002 | Spence et al. |
| 2002/0032481 A1 | 3/2002 | Gabbay |
| 2002/0052651 A1 | 5/2002 | Myers et al. |
| 2002/0058995 A1 | 5/2002 | Stevens |
| 2002/0077696 A1 | 6/2002 | Zadno-Azizi et al. |
| 2002/0095209 A1 | 7/2002 | Zadno-Azizi et al. |
| 2002/0111674 A1 | 8/2002 | Chouinard et al. |
| 2002/0151970 A1 | 10/2002 | Garrison et al. |
| 2002/0161392 A1 | 10/2002 | Dubrul |
| 2002/0161394 A1 | 10/2002 | Macoviak et al. |

| | | |
|---|---|---|
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0055495 A1 | 3/2003 | Pease et al. |
| 2003/0069635 A1 | 4/2003 | Cartledge et al. |
| 2003/0109924 A1 | 6/2003 | Cribier |
| 2003/0125795 A1 | 7/2003 | Pavcnik et al. |
| 2003/0125805 A1 | 7/2003 | Johnson et al. |
| 2003/0130729 A1 | 7/2003 | Paniagua et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0199913 A1 | 10/2003 | Dubrul et al. |
| 2003/0199963 A1 | 10/2003 | Tower et al. |
| 2003/0199972 A1 | 10/2003 | Zadno-Azizi et al. |
| 2003/0212452 A1 | 11/2003 | Zadno-Azizi et al. |
| 2003/0212454 A1 | 11/2003 | Scott et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0098112 A1 | 5/2004 | DiMatteo et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0186563 A1 | 9/2004 | Lobbi |
| 2004/0215339 A1 | 10/2004 | Drasler et al. |
| 2005/0075731 A1* | 4/2005 | Artof et al. ................ 623/2.18 |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096738 A1 | 5/2005 | Cali et al. |
| 2005/0209065 A1 | 9/2005 | Schlosser |
| 2005/0251251 A1 | 11/2005 | Cribier |
| 2006/0052867 A1 | 3/2006 | Revuelta et al. |
| 2007/0162107 A1* | 7/2007 | Haug et al. ................ 623/1.26 |

FOREIGN PATENT DOCUMENTS

| | | |
|---|---|---|
| EP | 0937439 B1 | 9/2003 |
| EP | 1340473 | 9/2003 |
| EP | 1356793 | 10/2003 |
| EP | 0810913 | 6/2004 |
| EP | 1229864 B1 | 4/2005 |
| FR | 2 826 863 | 1/2003 |
| WO | WO 93/15693 | 8/1993 |
| WO | WO 95/04556 | 2/1995 |
| WO | WO 95/29640 | 11/1995 |
| WO | WO 96/14032 | 5/1996 |
| WO | WO 98/36790 | 8/1998 |
| WO | WO 00/09059 | 2/2000 |
| WO | WO 00/44308 | 8/2000 |
| WO | WO 00/44313 | 8/2000 |
| WO | WO 00/67661 | 11/2000 |
| WO | WO 01/05331 | 1/2001 |
| WO | WO 01/35870 | 5/2001 |
| WO | WO 01/64137 | 9/2001 |
| WO | WO 02/36048 | 5/2002 |
| WO | WO 02/100297 | 12/2002 |
| WO | WO 03/003943 | 1/2003 |
| WO | WO 03/003949 | 1/2003 |
| WO | WO 03/011195 | 2/2003 |
| WO | WO 03/015851 | 2/2003 |
| WO | WO 2004/019811 | 3/2004 |
| WO | WO 2004/023980 | 3/2004 |
| WO | WO 2004/041126 | 5/2004 |
| WO | WO 2004/047681 | 6/2004 |
| WO | WO 2005/013860 | 2/2005 |

OTHER PUBLICATIONS

P. Bonhoeffer, MD et al., "Percutaneous Replacement of Pulmonary Valve in a Right-Ventricle to Pulmonary-Artery Prosthetic Conduit with Valve Dysfunction," pp. 1403-1405; Oct. 2000.

Y. Boudjemline, MD, et al., "Steps Towards Percutaneous Aortic Valve Replacement," pp. 775-778; Feb. 2002.

P. Bonhoeffer, MD, et al., "Percutaneous Insertion of the Pulmonary Valve," Journal of the American College of Carciology, vol. 39, No. 10, pp. 1664-1669; Feb. 2002.

A Cribier, MD, et al., "Percutaneous Transcatheter Implantation of an Aortic Valve Prosthesis for Calcific Aortic Stenosis—First Human Description," pp. 3006-3008; Dec. 2002.

A. Cribier, MD, et al.; "Early Experience with Percutaneous Transcatheter Implantation of Heart Valve Prosthesis for the Treatment of End-Stage Inoperable Patients with Calcific Aortic Stenosis," Journal of the American College of Cardiology, vol. 43, No. 4, pp. 698-703; Nov. 2003.

Y. Boudjemline, MD. et al., "Percutaneous Pulmonary Valve Replacement in a Large Right Ventricular Outflow Tract," Journal of the American College of Cardiology, vol. 43, No. 6; pp. 1082-1087; Mar. 2004.

Andersen, H.R. et al, "Tran luminal implantation of artificial heart valves. Description of a new expandable aortic valve and initial results with implantation by catheter technique in closed chest pigs." Euro. Heart J. (1992) 13:704-708.

Bonhoeffer, "Percutaneous insertion of the pulmonary valve," Journal of American College of Cardiology Foundation, (2002) 39(0):1664-1669.

Iliopoulos, et al., "Repeat replacement of aortic valve bioprosthesis," Ann. Thorac Surg. (1995), 59:1217-1219.

* cited by examiner

RIVETED STENT VALVE FOR PERCUTANEOUS USE

TECHNICAL FIELD

This invention relates generally to medical devices for treating cardiac valve abnormalities, and particularly to a pulmonary valve replacement system and method of employing the same.

BACKGROUND OF THE INVENTION

Heart valves, such as the mitral, tricuspid, aortic and pulmonary valves, are sometimes damaged by disease or by aging, resulting in problems with the proper functioning of the valve. Heart valve problems generally take one of two forms: stenosis, in which a valve does not open completely or the opening is too small, resulting in restricted blood flow; or insufficiency, in which blood leaks backward across a valve when it should be closed.

The pulmonary valve regulates blood flow between the right ventricle and the pulmonary artery, controlling blood flow between the heart and the lungs. Pulmonary valve stenosis is frequently due to a narrowing of the pulmonary valve or the pulmonary artery distal to the valve. This narrowing causes the right side of the heart to exert more pressure to provide sufficient flow to the lungs. Over time, the right ventricle enlarges, which leads to congestive heart failure (CHF). In severe cases, the CHF results in clinical symptoms including shortness of breath, fatigue, chest pain, fainting, heart murmur, and in babies, poor weight gain. Pulmonary valve stenosis most commonly results from a congenital defect, and is present at birth, but is also associated with rheumatic fever, endocarditis, and other conditions that cause damage to or scarring of the pulmonary valve. Valve replacement may be required in severe cases to restore cardiac function.

Previously, valve repair or replacement required open-heart surgery with its attendant risks, expense, and extended recovery time. Open-heart surgery also requires cardiopulmonary bypass with risk of thrombosis, stroke, and infarction. More recently, flexible valve prostheses and various delivery devices have been developed so that replacement valves can be implanted transvenously using minimally invasive techniques. As a consequence, replacement of the pulmonary valve has become a treatment option for pulmonary valve stenosis.

The most severe consequences of pulmonary valve stenosis occur in infants and young children when the condition results from a congenital defect. Frequently, the pulmonary valve must be replaced with a prosthetic valve when the child is young, usually less than five years of age. However, as the child grows, the valve can become too small to accommodate the blood flow to the lungs that is needed to meet the increasing energy demands of the growing child, and it may then need to be replaced with a larger valve. Alternatively, in a patient of any age, the implanted valve may fail to function properly due to calcium buildup and have to be replaced. In either case, repeated surgical or transvenous procedures are required.

To address the need for pulmonary valve replacement, various implantable pulmonary valve prostheses, delivery devices and surgical techniques have been developed and are presently in use. One such prosthesis is a bioprosthetic, valved conduit comprising a glutaraldehyde treated bovine jugular vein containing a natural, trileaflet venous valve, and sinus. A similar device is composed of a porcine aortic valve sutured into the center of a woven fabric conduit. A common conduit used in valve replacement procedures is a homograft, which is a vessel harvested from a cadaver. Valve replacement using either of these devices requires thoracotomy and cardiopulmonary bypass.

When the valve in the prostheses must be replaced, for the reasons described above or other reasons, an additional surgery is required. Because many patients undergo their first procedure at a very young age, they often undergo numerous procedures by the time they reach adulthood. These surgical replacement procedures are physically and emotionally taxing, and a number of patients choose to forgo further procedures after they are old enough to make their own medical decisions.

Recently, implantable stented valves have been developed that can be delivered transvenously using a catheter-based delivery system. These stented valves comprise a collapsible valve attached to the interior of a tubular frame or stent. The valve can be any of the valve prostheses described above, or it can be any other suitable valve. In the case of valves in harvested vessels, the vessel can be of sufficient length to extend beyond both sides of the valve such that it extends to both ends of the valve support stent.

The stented valves can also comprise a tubular portion or "stent graft" that can be attached to the interior or exterior of the stent to provide a generally tubular internal passage for the flow of blood when the leaflets are open. The graft can be separate from the valve and it can be made from any suitable biocompatible material including, but not limited to, fabric, a homograft, porcine vessels, bovine vessels, and equine vessels.

The stent portion of the device can be reduced in diameter, mounted on a catheter, and advanced through the circulatory system of the patient. The stent portion can be either self-expanding or balloon expandable. In either case, the stented valve can be positioned at the delivery site, where the stent portion is expanded against the wall of a previously implanted prostheses or a native vessel to hold the valve firmly in place.

One embodiment of a stented valve is disclosed in U.S. Pat. No. 5,957,949 titled "Percutaneous Placement Valve Stent" to Leonhardt, et al, the contents of which are incorporated herein by reference.

Typically, the valve is attached to the stent framework using sutures. One drawback of attaching the valve with sutures is that the process is labor intensive and costly. Another drawback to using sutures is that the sutures may be subject to abrasion near the stent struts. Continued abrasion of the sutures may lead to breakage of the suture and possible detachment of at lest a portion of the valve from the stent.

It would be desirable, therefore, to provide an implantable pulmonary valve that would overcome the limitations and disadvantages in the devices described above.

SUMMARY OF THE INVENTION

It is an object of the present invention to provide a valve replacement system having at least a delivery catheter and a replacement valve device disposed on the delivery catheter. The replacement valve device includes a prosthetic valve connected to a valve support region of an expandable support structure. The valve support region includes a plurality of protective struts disposed between a first stent region and a second stent region.

The system and the prosthetic valve will be described herein as being used for replacing a pulmonary valve. The pulmonary valve is also known to those having skill in the art as the "pulmonic valve" and as used herein, those terms shall be considered to mean the same thing.

Thus, one aspect of the present invention provides a pulmonary valve replacement system. The system comprises a conduit having an inner wall defining lumen and a replacement valve device. The replacement valve device includes a prosthetic valve connected to an expandable support structure; the expandable support structure includes at least one valve attachment portion and a plurality of valve attachment devices. Each valve attachment portion includes a plurality of struts, each strut having at least one opening for receiving one of the plurality of valve attachment devices.

Another aspect of the invention provides a system for treating a vascular condition comprising a conduit operably attached to a vessel, a delivery catheter and a replacement valve device disposed on the delivery catheter. The replacement valve device includes a prosthetic valve connected to an expandable support structure, the expandable support structure including at least one valve attachment portion and a plurality of valve attachment devices. Each valve attachment portion includes a plurality of struts, each strut having at least one opening for receiving one of the plurality of valve attachment devices.

Another aspect of the invention provides a method for treating a vascular condition. The method comprises inserting a conduit into a target region of a vessel and delivering a stented valve into the conduit lumen. The stented valve includes a prosthetic valve connected to an expandable support structure by a plurality of attachment devices, each attachment device having a head portion, a pin portion and a flange portion. The method further includes expanding the stented valve into contact with the inner wall of the conduit.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DESCRIPTION OF THE PRESENTLY PREFERRED EMBODIMENTS

The invention will now be described by reference to the drawings wherein like numbers refer to like structures.

Figure 1:
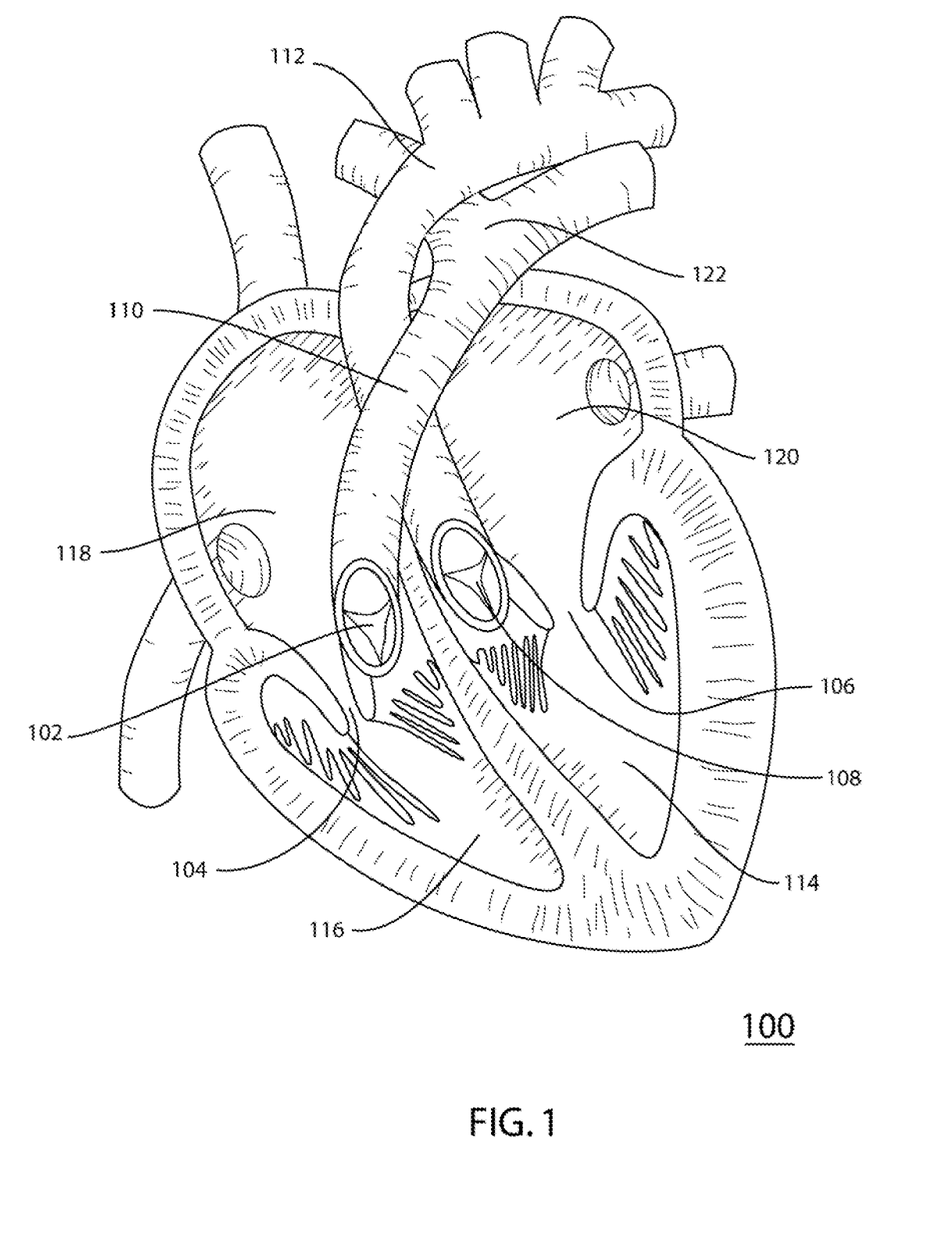
FIG. 1 is a schematic interior view of a human heart showing the functioning of the four heart valves.

Referring to the drawings, FIG. 1 is a schematic representation of the interior of human heart 100. Human heart 100 includes four valves that work in synchrony to control the flow of blood through the heart. Tricuspid valve 104, situated between right atrium 118 and right ventricle 116, and mitral valve 106, between left atrium 120 and left ventricle 114 facilitate filling of ventricles 116 and 114 on the right and left sides, respectively, of heart 100. Aortic valve 108 is situated at the junction between aorta 112 and left ventricle 114 and facilitates blood flow from heart 100, through aorta 112 to the peripheral circulation.

Pulmonary valve 102 is situated at the junction of right ventricle 116 and pulmonary artery 110 and facilitates blood flow from heart 100 through the pulmonary artery 110 to the lungs for oxygenation. The four valves work by opening and closing in harmony with each other. During diastole, tricuspid valve 104 and mitral valve 106 open and allow blood flow into ventricles 114 and 116, and the pulmonic valve and aortic valve are closed. During systole, shown in FIG. 1, aortic valve 108 and pulmonary valve 102 open and allow blood flow from left ventricle 114, and right ventricle 116 into aorta 112 and pulmonary 110, respectively.

The right ventricular outflow tract is the segment of pulmonary artery 110 that includes pulmonary valve 102 and extends to branch point 122, where pulmonary artery 110 forms left and right branches that carry blood to the left and right lungs respectively. A defective pulmonary valve or other abnormalities of the pulmonary artery that impede blood flow from the heart to the lungs sometimes require surgical repair or replacement of the right ventricular outflow tract with prosthetic conduit 202, as shown in FIG. 2A-C.

Such conduits comprise tubular structures of biocompatible materials, with a hemocompatible interior surface. Examples of appropriate biocompatible materials include polytetrafluoroethylene (PTFE), woven polyester fibers such as Dacron® fibers (E.I. Du Pont De Nemours & Co., Inc.), and bovine vein cross linked with glutaraldehyde. One common conduit is a homograft, which is a vessel harvested from a cadaver and treated for implantation into a recipient's body. These conduits may contain a valve at a fixed position within the interior lumen of the conduit that functions as a replacement pulmonary valve.

One such conduit 202 comprises a bovine jugular vein with a trileaflet venous valve preserved in buffered glutaraldehyde. Other valves are made of xeno-pericardial tissue and are attached to the wall of the lumen of the conduit. Still other valves may be made at least partially from some synthetic material. The conduits may also include materials having a high X-ray attenuation coefficient (radiopaque materials) that are woven into or otherwise attached to the conduit, so that it can be easily located and identified.

Figure 2A:
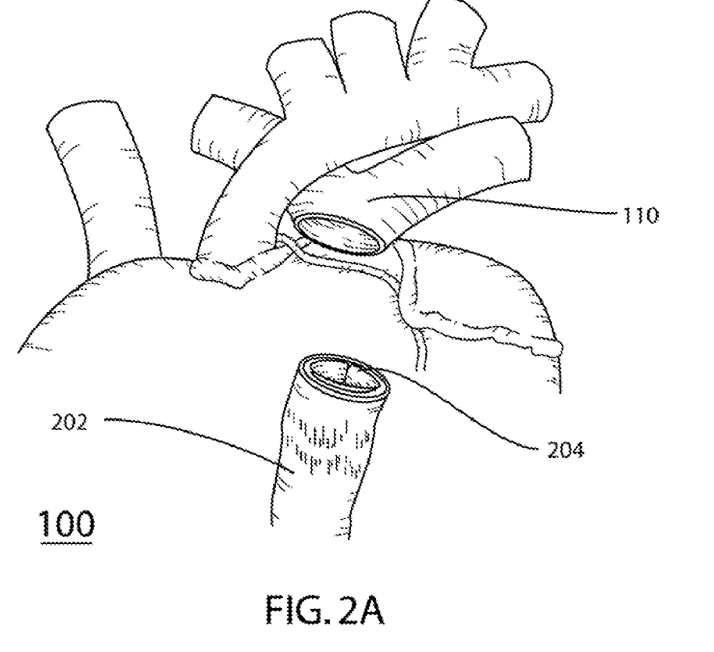
FIG. 2A is a schematic view showing the placement of a pulmonary conduit, as is known in the prior art.
Figure 2B:
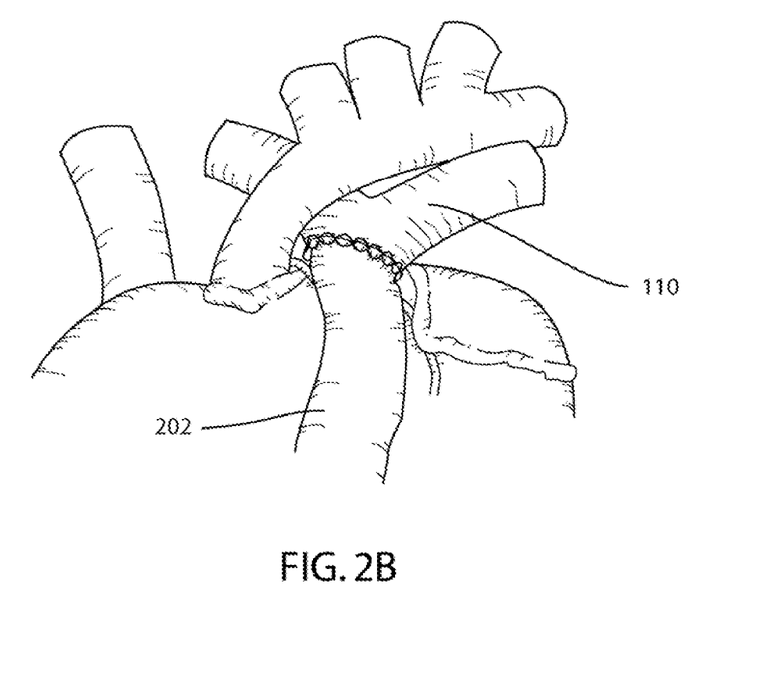
FIG. 2B is a schematic view showing attachment of a pulmonary conduit to the pulmonary artery, as is known in the prior art.
Figure 2C:
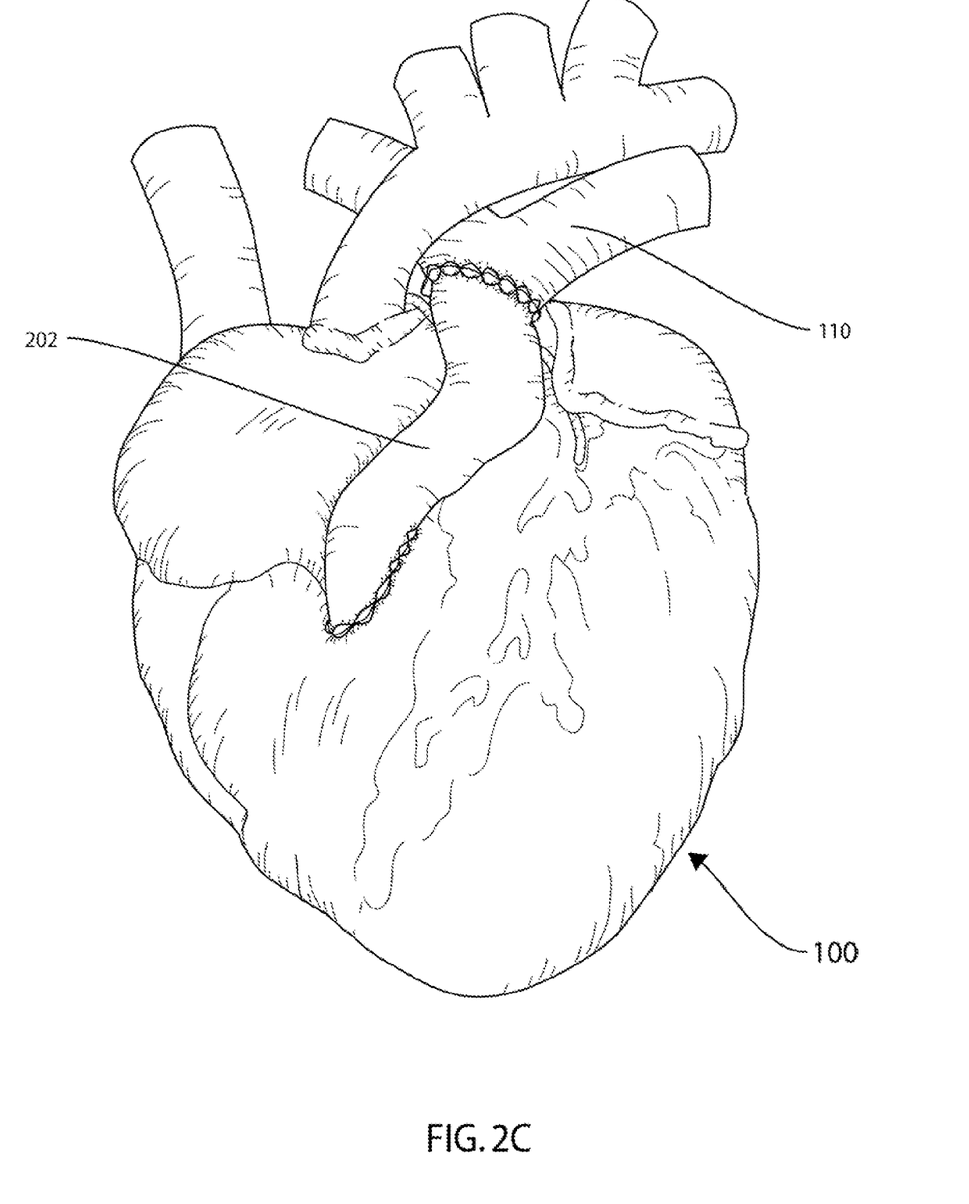
FIG. 2C is a schematic view showing attachment of a pulmonary conduit to the heart, as is known in the prior art.

As shown in FIGS. 2A and 2B, conduit 202, which houses valve 204 within its inner lumen, is installed within a patient by sewing the distal end of conduit 202 to pulmonary artery 110, and, as shown in FIG. 2C, attaching the proximal end of conduit 202 to heart 100 so that the lumen of conduit 202 connects to right ventricle 116.

Over time, implanted prosthetic conduits and valves are frequently subject to calcification, causing the affected conduit or valve to lose flexibility, become misshapen, and lose the ability to function effectively. Additional problems are encountered when prosthetic valves are implanted in young children. As the child grows, the valve will ultimately be too small to handle the increased volume of blood flowing from the heart to the lungs. In either case, the valve needs to be replaced.

The current invention discloses devices and methods for percutaneous catheter based placement of stented valves for regulating blood flow through a pulmonary artery. In a preferred embodiment, the valves are attached to an expandable support structure and they are placed in a valved conduit that is been attached to the pulmonary artery, and that is in fluid communication with the right ventricle of a heart. The support structure can be expanded such that any pre-existing valve in the conduit is not disturbed, or it can be expanded such that any pre-existing valve is pinned between the support structure and the interior wall of the conduit.

The delivery catheter carrying the stented valve is passed through the venous system and into a patient's right ventricle. This may be accomplished by inserting the delivery catheter into either the jugular vein or the subclavian vein and passing it through superior vena cava into right atrium. The catheter is then passed through the tricuspid valve, into right ventricle, and out of the ventricle into the conduit. Alternatively, the catheter may be inserted into the femoral vein and passed through the common iliac vein and the inferior vena cava into the right atrium, then through the tricuspid valve, into the right ventricle and out into the conduit. The catheters used for the procedures described herein may include radiopaque markers as are known in the art, and the procedure may be visualized using fluoroscopy, echocardiography, ultrasound, or other suitable means of visualization.

Figure 3:
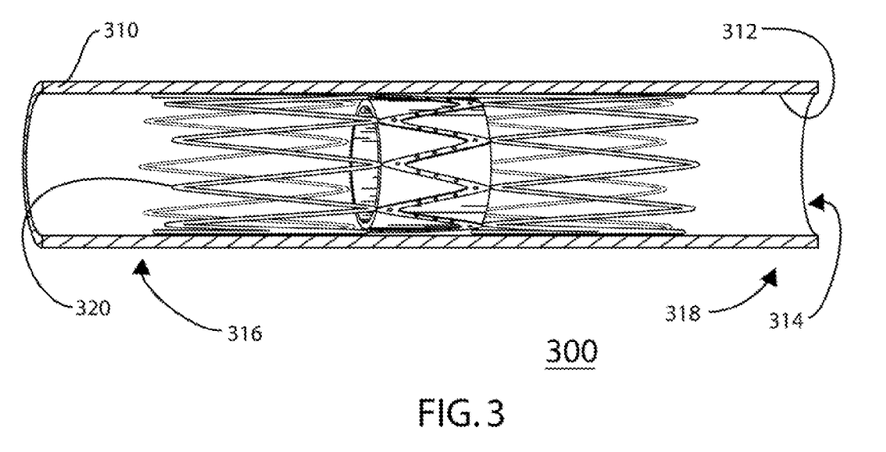
FIG. 3 is a schematic view of one embodiment of a prosthetic valve device situated in a conduit, in accordance with the present invention.

FIG. 3 illustrates a cross section of one embodiment of a system 300 for treating a vascular condition within heart 100 illustrated in FIG. 1. System 300 illustrated in FIG. 3 is described herein with reference to a bioprosthetic conduit for replacing a portion of a pulmonary artery. Those with skill in the art will recognize that the invention may be adapted to other vessels of a body that require a replacement valve.

System 300 is illustrated in an expanded configuration as it would appear in place within a bioprosthetic conduit. System 300 comprises a bioprosthetic conduit 310 and a stented valve 320. Conduit 310 comprises an elongate tubular structure that includes an inner wall 312 that defines a lumen 314. Lumen 314 allows fluid communication between the right ventricle and the pulmonary artery. Conduit 310 includes a first end 316 for attaching to ventricle 110 and a second end 318 for attaching to pulmonary artery 122.

Figure 4:
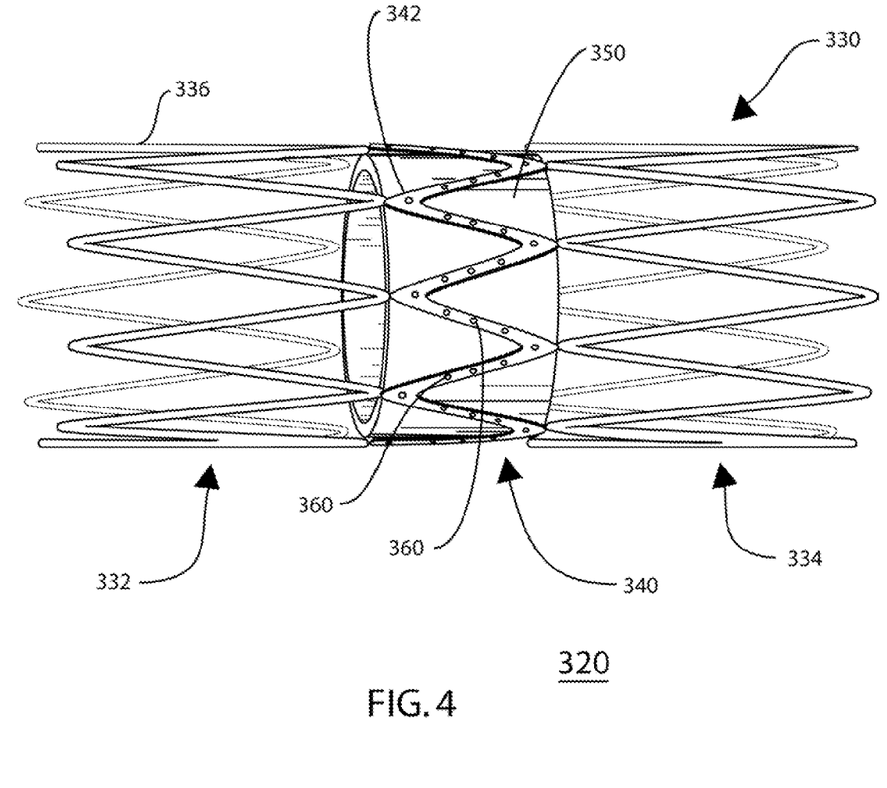
FIG. 4 is a schematic view of one embodiment of a prosthetic valve device, in accordance with the present invention.

Referring to FIG. 4, stented valve 320 comprises a stent framework 330 and a prosthetic valve 350. In one embodiment of the invention, stent framework 330 is a stent made of a flexible, biocompatible material that has "shape memory." The stent framework 330 may be composed of self-expanding material and manufactured from, for example, a nickel titanium alloy and/or other alloy(s) that exhibit superelastic behavior. Other suitable materials for stent framework 330 include, but are not limited to, a nitinol alloy, a stainless steel, a cobalt-based alloy, and an MP35N® alloy. Furthermore, the stent framework material may include polymeric biocompatible materials recognized in the art for such devices.

Stent framework 330 comprises a first stent region 332, a second stent region 334 and a valve support region 340 disposed between the first stent region 332 and the second stent region 334. Valve support region 340 comprises a stent framework composed of a plurality of valve support struts 342. First stent region 332 and second stent region 334 each comprise a stent framework composed of a plurality of struts 336.

In one embodiment, prosthetic valve 350 comprises a bovine jugular vein with a trileaflet venous valve preserved in buffered glutaraldehyde. In other embodiments, prosthetic valve 350 comprises a valve made of synthetic materials and attached to the stent framework 330. Prosthetic valve 350 is operably attached to valve support region 340 of the stent framework 330 by a plurality of valve attachment devices 360 disposed within a plurality of strut openings 348.

Figure 5:
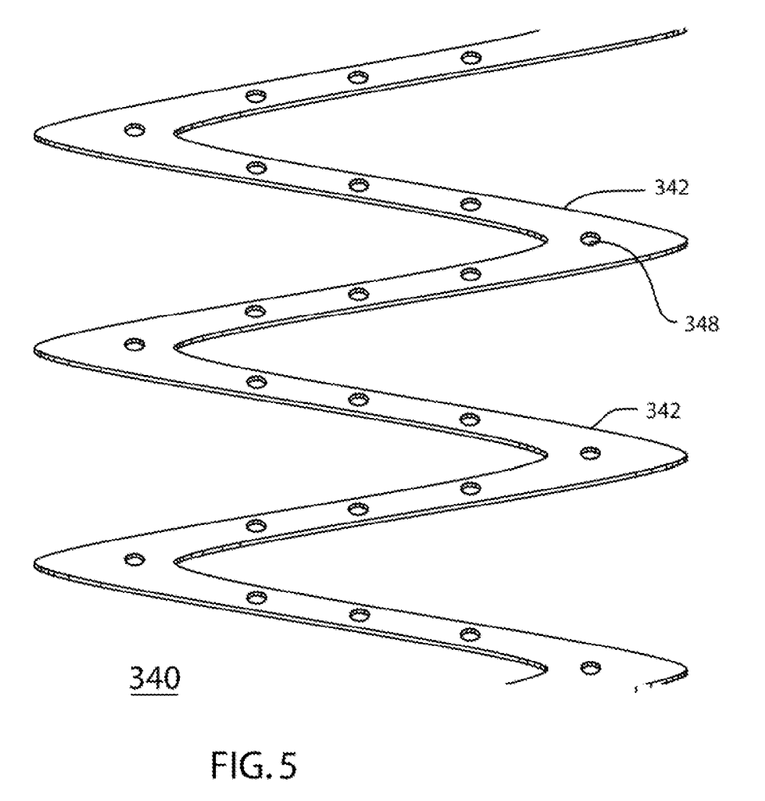
FIG. 5 is a schematic view showing a detailed portion of the device illustrated in FIG. 4.
Figure 8:
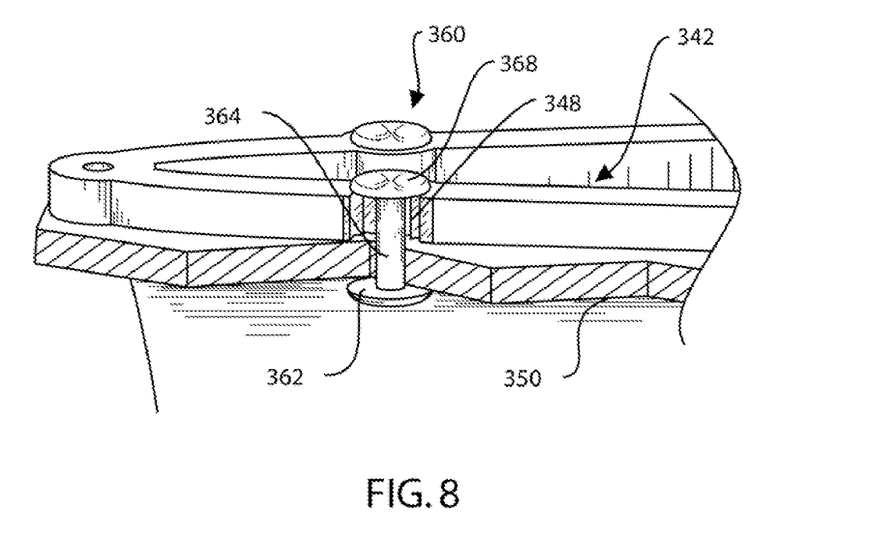
FIG. 8 is a detailed view of one embodiment of an attachment device, in accordance with the present invention.

Referring to FIG. 5, there is illustrated a detailed view of valve support region 340. As illustrated, valve support region 340 comprises a plurality of strut members 342. In this embodiment, each strut member 342 includes a plurality of strut openings 348. Strut openings 348 are sized to receive one of the attachment devices 360. Strut openings 348 are spaced apart along strut member 342. Strut openings may be formed in the strut members by any means known in the art. In one embodiment, strut openings are laser cut. In other embodiments, the strut openings are drilled or stamped into the strut members. Those with skill in the art will recognize that the location and number of strut openings may vary depending on the application. For example, the location and number of openings may depend on factors such as, the size of the strut and the size of the valve to be secured to the valve support. Referring to FIG. 8, FIG. 8 illustrates one embodiment of an attachment device 360 for securing prosthetic valve 350 to valve support 340.

In one embodiment, attachment device 360 comprises a rivet device and the prosthetic valve is secured to the stent framework by a plurality of the devices. In one embodiment, a stent graft is also secured to the stent framework by a plurality of rivet devices. In another embodiment, attachment device 360 comprises a head portion 362, a pin portion 364 and a flange portion 368. Attachment device 360 is made of a flexible, biocompatible material that has "shape memory." Suitable materials for attachment device 360 include, but are not limited to, a nitinol alloy, a stainless steel, a cobalt-based alloy, an MP35N® alloy or a combination thereof.

Head portion 362 comprises a broad flat head configured in a nail-head like fashion. In one embodiment, head portion 362 is configured to include rounded edges on at least those edges that are in contact with the prosthetic valve. In another embodiment, head portion 362 includes comprises a radiopaque material to aid in the visualization of the stented valve during implantation. In one embodiment, head portion includes materials having a high X-ray attenuation coefficient (radiopaque materials) so that the stented valve 320 can be easily located and positioned within conduit 310. The head portion may include radiopaque metals such as, for example, gold and platinum.

Pin portion 364 extends perpendicularly to head portion 362. Pin portion 364 may comprise a hollow tube or a solid cylinder. In one embodiment, pin portion 364 includes a sharp end portion configured for tissue penetration. In one embodiment, pin portion 364 is configured to penetrate prosthetic valve 350 during attachment of the prosthetic valve 350 to valve support region 340 of the stent framework 330.

In one embodiment, flange portion 368 extends from pin portion 364. In one embodiment, flange portion 368 comprises a shape memory material that in a first configuration, (an insertion configuration), is sized to pass through opening 348 and after insertion forms a flange to assume a second configuration, (an attachment configuration), that is unable to pass back through opening 348.

Figure 10A:
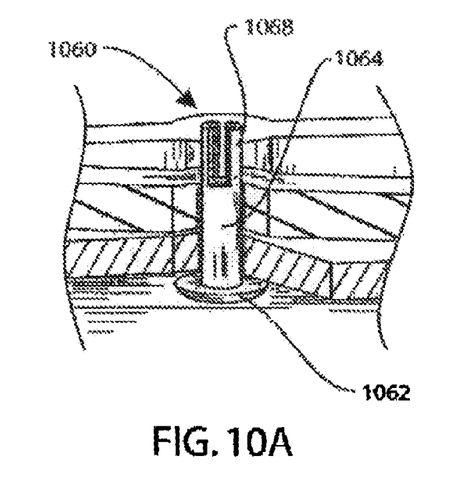
FIGS. 10A to 10B is a schematic view of one embodiment of an attachment device, in accordance with the present invention.
Figure 10B:
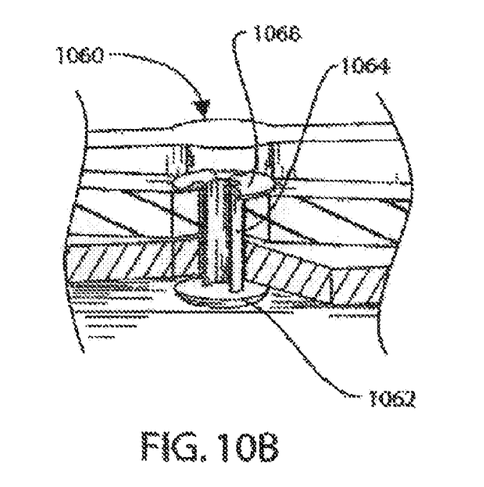

FIGS. 10A and 10B illustrate one embodiment of an attachment device 1060 for securing a prosthetic valve to a stent framework. Attachment device 1060 comprises a head portion 1062, a pin portion 1064 and a flange portion 1068. FIG. 10A illustrates the attachment device 1060 where the flange portion 1068 is in an insertion configuration and FIG. 10B illustrates the attachment device 1060 where the flange portion 1068 is in an attachment configuration.

Figure 11A:
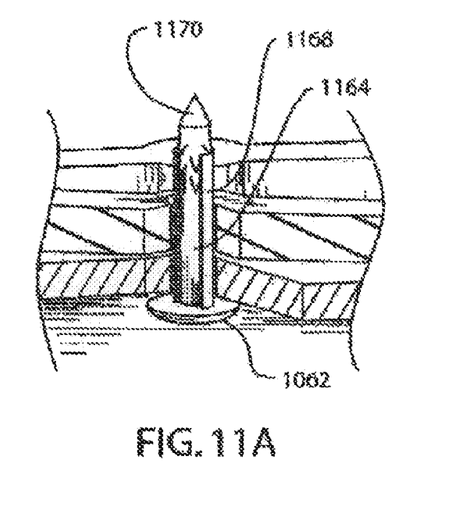
FIGS. 11A to 11B is a schematic view of one embodiment of an attachment device, in accordance with the present invention.
Figure 11B:
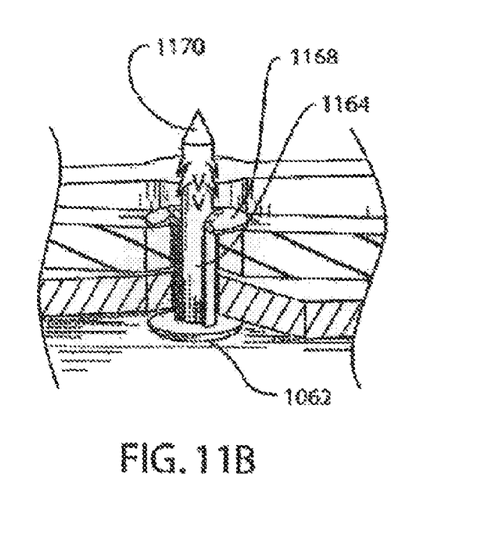

FIGS. 11A and 11B illustrate another embodiment of an attachment device 1160 for securing a prosthetic valve to a stent framework. Attachment device 1160 comprises a head portion 1162, a pin portion 1164 and a flange portion 1168. In this embodiment, pin portion 1164 includes a barbed end portion 1070. Barbed end portion 1070 is configured to penetrate the inner wall 312 of the prosthetic conduit 310 upon expansion of the stented valve into contact with the conduit. In one embodiment, barbed end portion comprises a shape memory material such as, for example, nitinol. In one embodiment, flange portion 1168 comprises a sleeve operably attached to the outer surface of pin portion 1164. In another embodiment, pin portion 364 comprises a core portion that forms barb 1070 and an outer portion that forms flange portion 1168. In one embodiment, barbed end portion 1070 anchors the stented valve in the conduit to prevent or reduce migration of the valve along the conduit after implantation.

Returning to FIG. 8, an attachment device 360 is illustrated in the attachment configuration. During manufacture of the stented valve, the prosthetic valve 350 is positioned within the lumen of the stent framework 330 in the desired location. Then, to secure the prosthetic valve 350 to the valve support region 340 of stent framework 330 the end of the pin portion opposite the head portion is aligned with one of the plurality of stent openings and the pin portion is passed through the tissue of the prosthetic valve and through the stent opening. Once the end of the pin portion is through the stent opening the flange portion assumes the attachment configuration, such as the attachment configurations illustrated in FIGS. 8, 10B and 11B.

Figure 9:
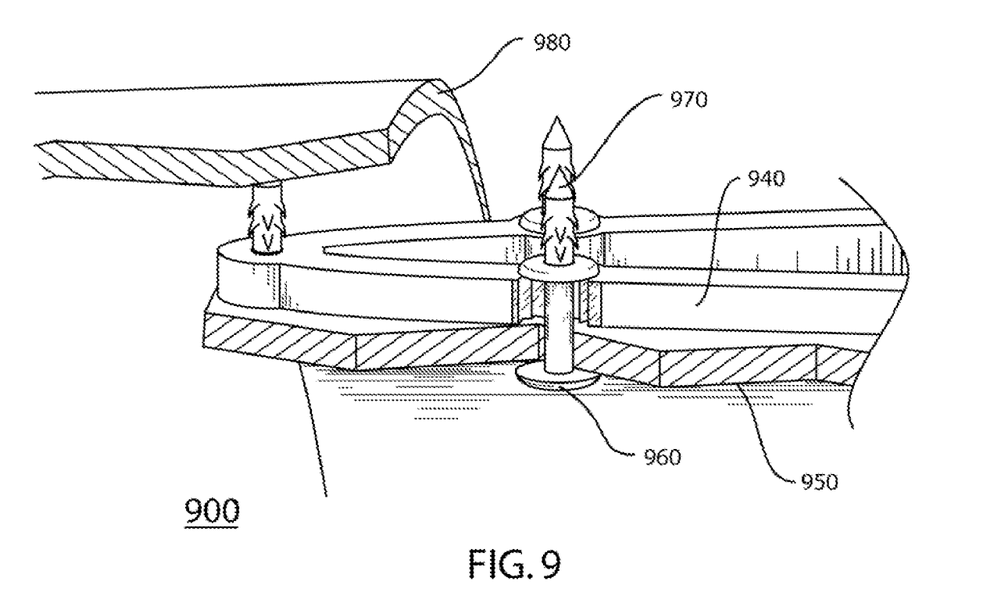
FIG. 9 is a detailed view of one embodiment of an attachment device, in accordance with the present invention.

Referring to FIG. 9, FIG. 9 illustrates a detailed view of a portion of one embodiment of a stented valve 900 having an attachment device 960 for securing prosthetic valve 950 to valve support 940. In one embodiment, attachment device 960 comprises the attachment device 1160 illustrated in FIGS. 11A and 11B. In one embodiment, the stented valve 900 comprises a self-expanding stent framework. During delivery of the self-expanding stented valve 900 to the treatment site, the stented valve is restrained using a retractable sheath 980. Retractable sheath 980 also restrains barbs 970 and prevents the barbs from contacting the inner walls of the patient's vasculature during delivery of the stented valve to the treatment site. In one embodiment, barbs 970 are comprises of a resilient material having shape memory. In one embodiment, barbs 970 are delivered to the treatment site in a bent delivery configuration, and upon retraction of sheath 980 assume a substantially straight insertion configuration, as shown.

Figure 6:
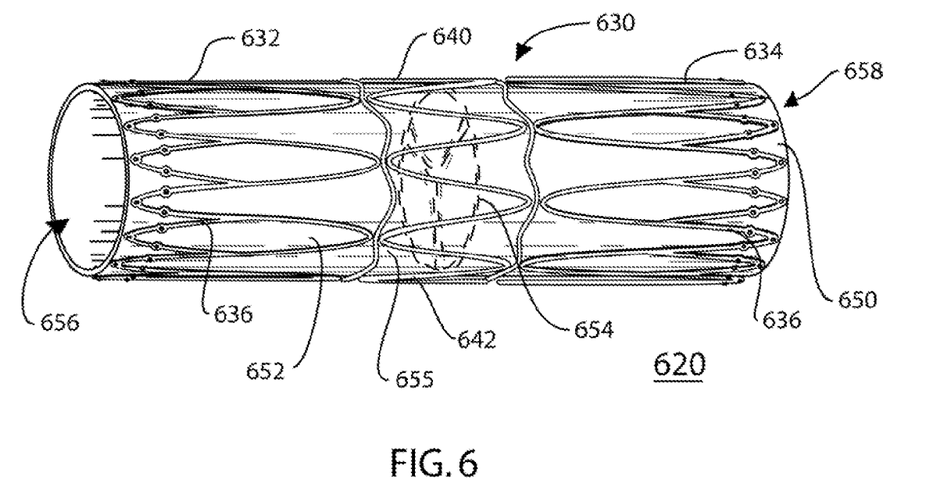
FIG. 6 is a schematic view of another embodiment of a prosthetic valve device, in accordance with the present invention.

Referring to FIG. 6, stented valve 620 comprises a stent framework 630 and a prosthetic valve 650. In one embodiment of the invention, stent framework 630 is a stent made of a flexible, biocompatible material that has "shape memory." The stent framework 630 may be composed of self-expanding material and manufactured from, for example, a nickel titanium alloy and/or other alloy(s) that exhibit superelastic behavior. Other suitable materials for stent framework 630 include, but are not limited to, a nitinol alloy, a stainless steel, a cobalt-based alloy, and an MP35N® alloy. Furthermore, the stent framework material may include polymeric biocompatible materials recognized in the art for such devices.

Stent framework 630 comprises a first stent region 632, a second stent region 634 and a valve support region 640 disposed between the first stent region 632 and the second stent region 634. Valve support region 640 comprises a stent framework composed of a plurality of valve support struts 642. First stent region 632 and second stent region 634 each comprise a stent framework composed of a plurality of valve end support struts 636.

In one embodiment, prosthetic valve 650 comprises a bovine jugular vein with a trileaflet venous valve preserved in buffered glutaraldehyde. In other embodiments, prosthetic valve 650 comprises a valve made of synthetic materials and attached to the stent framework 630. In this embodiment, prosthetic valve 650 comprises an elongate body portion 652 having a centrally located valve 654 within central region 655. Elongate body portion has a first end 656 and a second end 658. In this embodiment, a central region 655 of prosthetic valve 650 is attached to the stent framework 630 at valve support region 640 by a plurality of valve attachment devices 660. In one embodiment, valve support region is the same as or similar to that described above and illustrated in FIG. 5. Attachment devices 660 used for securing central region 655 to valve support region 640 may be similar to or the same as those described above and illustrated in FIGS. 8 to 11B.

First end 656 of prosthetic valve 650 is attached to first stent region 632 and second end 658 is attached to second stent region 634 by a plurality of valve attachment devices 660. Attachment devices 660 may be similar to or the same as those described above and illustrated in FIGS. 8 to 11B.

Figure 7:
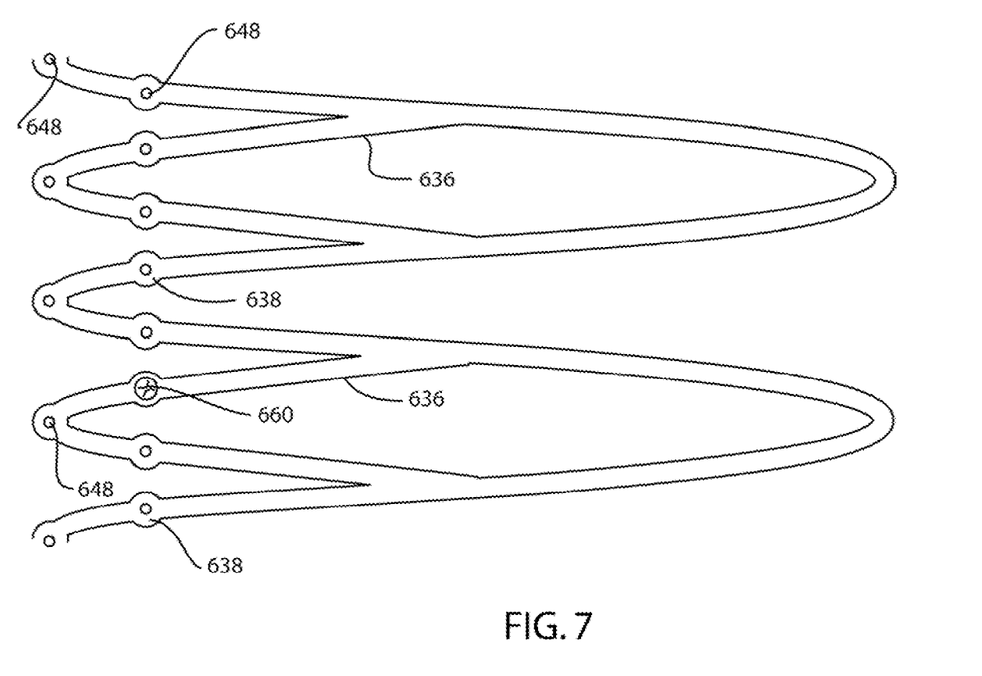
FIG. 7 is a schematic view showing a detailed portion of the device illustrated in FIG. 6.

Referring to FIG. 7 there is a detailed view of the valve end support struts 636 located at the outer stent framework for both the first stent region 632 and the second stent region 634. First stent region 632 and second stent region comprise a plurality of struts. In one embodiment the plurality of struts include valve end support struts 636. Valve end support struts 636 are located adjacent the ends of the stent framework to provide attachment support to the ends of the stented valve. In one embodiment, the apex of each strut comprising the first and second stent region includes a valve end support strut 636. Each valve end support strut 636 includes at least one strut opening 648. Strut openings 648 are sized to receive one of the attachment devices 660. In one embodiment, strut openings 648 are spaced apart along strut 636. Strut openings may be formed in the strut members by any means known in the art. In one embodiment, strut openings are laser cut.

In other embodiments, the strut openings are drilled or stamped into the strut members. Those with skill in the art will recognize that the location and number of strut openings may vary depending on the application. For example, the location and number of openings may depend on factors such as, the size of the strut and the size of the prosthetic valve to be secured to the valve support. In one embodiment, the valve end support strut includes an enlarged region 638 around each of the strut openings 648. Enlarged regions 638 of the valve end support struts 636 provide an increased surface for supporting the tissue of the prosthetic valve when sandwiched between the strut surface and the head of the attachment device 660.

Figure 12:
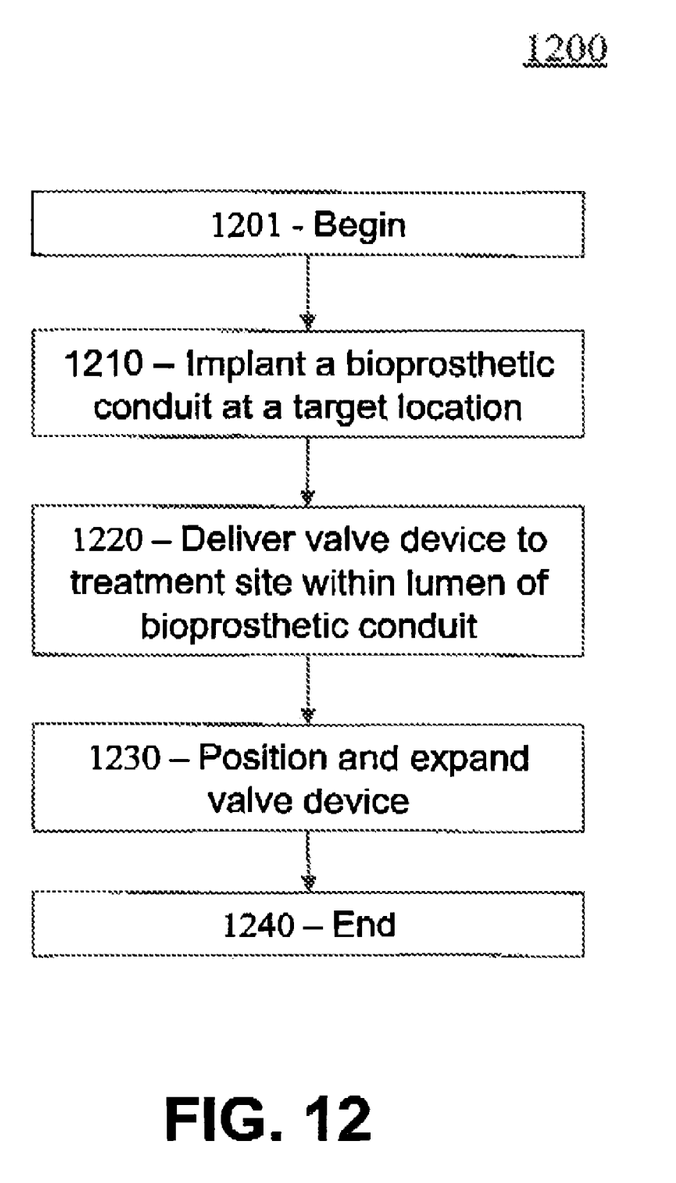
FIG. 12 is a flow diagram of one embodiment of a method of treating a vascular condition in accordance with the present invention.

FIG. 12 is a flowchart illustrating method 1200 for treating right ventricular outflow tract abnormalities by replacing a pulmonary valve, in accordance with the present invention. Method 1200 begins at step 1201. At step 1210, a bioprosthetic conduit is implanted into a target region of a vessel.

Next, a stented valve is delivered into a target site within a lumen of the bioprosthetic conduit, at step 1220. In one embodiment, the stented valve is delivered percutaneously via a delivery catheter as are known in the art. In one embodiment, the target site within the conduit lumen comprises that portion of the lumen containing a pulmonary valve.

At step 1230, the stented valve is expanded to position the stented valve within the conduit lumen. In one embodiment, the stented valve is expanded into position using a balloon. In another embodiment, the stented valve comprises a self-expanding stent that expands radially when released from the delivery catheter. In one embodiment, the stented valve expands radially when released from a restraining sheath of the delivery catheter. In another embodiment, withdrawal of the restraining sheath deploys a plurality of barbs into a penetration configuration. In one embodiment, expansion of the self expanding stented valve sets the barbs within the wall of the prosthetic conduit or vessel. In another embodiment, the barbs are set using an inflation device deployed within the stented valve after delivery. Contact of the balloon with the head of the attachment device drives the attached barb into the wall of the conduit, thereby securing the stented valve to the conduit. Method 1200 ends at 1240.

While the invention has been described with reference to particular embodiments, it will be understood by one skilled in the art that variations and modifications may be made in form and detail without departing from the spirit and scope of the invention.

What is claimed is:

1. A vascular valve replacement system, the system comprising:
   a replacement valve device, the replacement valve device including a prosthetic valve connected to an expandable support structure, the expandable support structure including at least one valve attachment portion, each valve attachment portion having a plurality of struts, and each strut having at least one opening for receiving a valve attachment device; and
   a plurality of valve attachment devices;
   wherein the valve attachment device comprises a head portion, a pin portion and a flange portion and wherein the flange portion comprises a shape memory material, the flange portion having a delivery configuration and an attachment configuration.

2. The system of claim 1 wherein the pin portion includes a barb.

3. The system of claim 1 wherein the expandable support structure further comprises a first stent region and a second stent region, the at least one valve attachment portion disposed between the first stent region and the second stent region.

4. The system of claim 3 wherein the first stent region and the second stent region include a plurality of valve end support struts.

5. The system of claim 4 wherein each of the plurality of valve end support struts include at least one opening for receiving one of the plurality of valve attachment devices.

6. The system of claim 1 wherein at least a portion of the valve attachment device comprises a radiopaque material.

7. The system of claim 1 wherein the expandable support structure comprises a self-expanding stent.

8. The system of claim 1 wherein the expandable support structure comprises a balloon expandable stent.

9. A system for treating a vascular condition, comprising:
   a conduit operably attached to a vessel, the conduit including an inner wall defining a lumen;
   a delivery catheter;
   a replacement valve device disposed on the delivery catheter, the replacement valve device including a prosthetic valve connected to an expandable support structure, the expandable support structure including at least one valve attachment portion; and
   a plurality of valve attachment devices,
   wherein each valve attachment portion includes a plurality of struts, each strut having at least one opening for receiving one of the plurality of valve attachment devices,
   wherein the valve attachment device comprises a head portion, a pin portion and a flange portion, and
   wherein the pin portion includes a barb for penetrating the inner wall of the conduit.

10. The system of claim 9 wherein the expandable support structure further comprises a first stent region and a second stent region, the at least one valve attachment portion disposed between the first stent region and the second stent region.

11. The system of claim 10 wherein the first stent region and the second stent region include a plurality of valve end support struts.

12. The system of claim 11 wherein each of the plurality of valve end support struts include at least one opening for receiving one of the plurality of valve attachment devices.

13. The system of claim 9 wherein the expandable support structure comprises a self-expanding stent.

14. The system of claim 9 wherein the expandable support structure comprises a balloon expandable stent.

15. A system for treating a vascular condition, comprising:
   a conduit operably attached to a vessel, the conduit including an inner wall defining a lumen;
   a delivery catheter;
   a replacement valve device disposed on the delivery catheter, the replacement valve device including a prosthetic valve connected to an expandable support structure, the expandable support structure including at least one valve attachment portion; and
   a plurality of valve attachment devices,
   wherein each valve attachment portion includes a plurality of struts, each strut having at least one opening for receiving one of the plurality of valve attachment devices,
   wherein the valve attachment device comprises a head portion, a pin portion and a flange portion, and
   wherein the flange portion comprises a shape memory material, the flange portion having a delivery configuration and an attachment configuration.

16. A method for treating a vascular condition, the method comprising:
   inserting a conduit into a target region of a vascular system, the conduit having an inner wall defining a conduit lumen;
   delivering a stented valve into the conduit lumen, the stented valve including a prosthetic valve connected to an expandable support structure by a plurality of attachment devices each attachment device having a head portion, a pin portion and a flange portions wherein the flange portion comprises a shape memory material, the flange portion having a delivery configuration and an attachment configuration, the expandable support structure including at least one valve attachment portion, each valve attachment portion having a plurality of struts, and each strut having at least one opening for receiving a valve attachment device; and expanding the stented valve into contact with the inner wall of the conduit.

17. The system of claim 15 wherein the expandable support structure further comprises a first stent region and a second stent region, the at least one valve attachment portion disposed between the first stent region and the second stent region.

18. The system of claim 17 wherein the first stent region and the second stent region include a plurality of valve end support struts.

19. The system of claim 18 wherein each of the plurality of valve end support struts include at least one opening for receiving one of the plurality of valve attachment devices.

* * * * *

UNITED STATES PATENT AND TRADEMARK OFFICE
CERTIFICATE OF CORRECTION

| | |
|---|---|
| PATENT NO. | : 7,591,848 B2 |
| APPLICATION NO. | : 11/278856 |
| DATED | : September 22, 2009 |
| INVENTOR(S) | : Jeffrey W. Allen |

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 334 days.

should read (*) Notice: Subject to any disclaimer, the term of this patent is extended or adjusted under 35 U.S.C. 154(b) by 439 days.

Column 11, line 1, "flange portions" should be changed to --flange portion--.

Signed and Sealed this

Twenty-second Day of June, 2010

David J. Kappos
*Director of the United States Patent and Trademark Office*